United States Patent [19]

Johnson

[11] 4,210,748
[45] Jul. 1, 1980

[54] ENLARGED-HETERO-RING PROSTA-CYCLIN ANALOGS

[75] Inventor: Roy A. Johnson, Kalamazoo, Mich.

[73] Assignee: The Upjohn Company, Kalamazoo, Mich.

[21] Appl. No.: 932,899

[22] Filed: Aug. 11, 1978

Related U.S. Application Data

[60] Division of Ser. No. 819,856, Jul. 28, 1977, Pat. No. 4,123,441, which is a continuation-in-part of Ser. No. 725,546, Sep. 22, 1976, abandoned, which is a continuation-in-part of Ser. No. 716,960, Aug. 23, 1976, abandoned.

[51] Int. Cl.² .......................................... C07D 311/02
[52] U.S. Cl. ................... 542/426; 260/345.2
[58] Field of Search .............. 260/345.2, 346.22; 542/426, 439, 447, 429

[56] References Cited

PUBLICATIONS

Pace-Asciak et al., JACS, 98, 2348 (1976).
Pace-Asciak et al., Biochem., 10, 3657 (1971).

Primary Examiner—Nicky Chan
Attorney, Agent, or Firm—Robert A. Armitage; Morris L. Nielsen

[57] ABSTRACT

Prostaglandin ($PG_1$) derivatives having (1) a 5-keto feature, for example

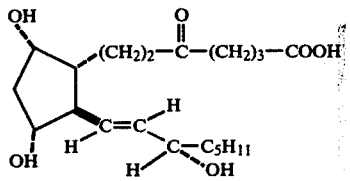

or (2) a 9-deoxy-5,9-epoxy feature together with a 4-halo or 5-hydroxy feature, for example

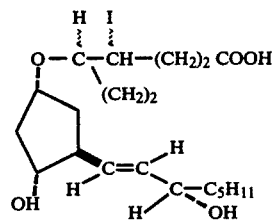

or

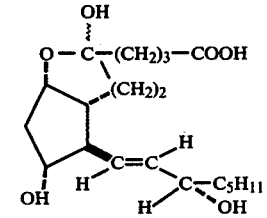

or a 4,5-didehydro feature, for example in an enol ether of the formula

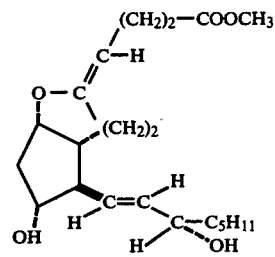

said derivatives having pharmacological activity. Processes for preparing them and the appropriate intermediates are disclosed.

97 Claims, No Drawings

ENLARGED-HETERO-RING PROSTA-CYCLIN ANALOGS

CROSS REFERENCE TO RELATED APPLICATIONS

This application is a division of copending application Ser. No. 819,856 filed July 28, 1977 now issued as U.S. Pat. No. 4,123,441, which was a continuation-in-part of then copending application Ser. No. 725,546 filed Sept. 22, 1976, since abandoned, which was a continuation-in-part of then copending application Ser. No. 716,960 filed Aug. 23, 1976, since abandoned.

BACKGROUND OF THE INVENTION

This invention relates to prostaglandin derivatives and to a process for preparing them.

Some of the compounds of this invention may be regarded as analogs of prostacyclin and prostacyclin-type compounds.

The essential material for this application, including the background of the invention, the disclosure of the invention, and the description of the preferred embodiments, including Preparations and Examples, is incorporated by reference from issued U.S. Pat. No. 4,123,441 under the provisions of M.P.E.P. 608.01(p).

SUMMARY OF THE INVENTION

It is the purpose of this invention to provide novel products having pharmacological activity. It is a further purpose to provide processes for preparing these products and their intermediates.

Accordingly, there is provided a compound of the formula:

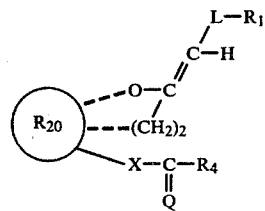
IV wherein 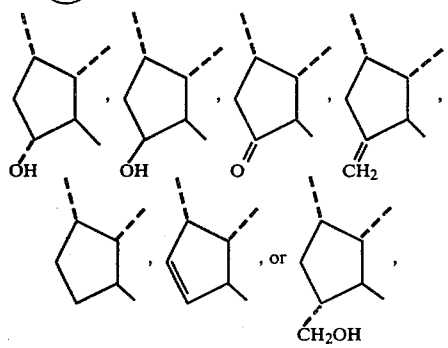 is wherein L is
(1) —(CH$_2$)$_d$—C(R$_2$)$_2$—
(2) —O—CH$_2$—Y— or
(3) —CH=CH— wherein d is zero to 5, R$_2$ is hydrogen, methyl, or fluoro, being the same or different with the proviso that one R$_2$ is not methyl when the other is fluoro, and Y is a valence bond, —CH$_2$— or —(CH$_2$)$_2$—, wherein Q is

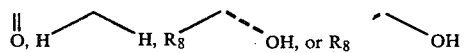

wherein R$_8$ is hydrogen or alkyl of one to 4 carbon atoms, inclusive,
wherein R$_1$ is
(1) —COOR$_3$
(2) —CH$_2$OH
(3) —CH$_2$N(R$_9$)(R$_{18}$)

 (4)

 (5)

wherein R$_3$ is (a) hydrogen, (b) alkyl of one to 12 carbon atoms, inclusive, (c) cycloalkyl of 3 to 10 carbon atoms, inclusive, (d) aralkyl of 7 to 12 carbon atoms, inclusive (e) phenyl, (f) phenyl substituted with one, 2, or 3 chloro or alkyl of one to 4 carbon atoms, inclusive,

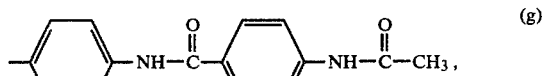 (g)

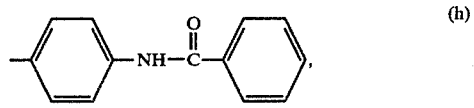 (h)

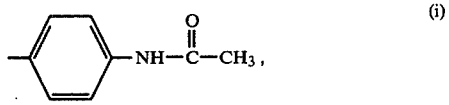 (i)

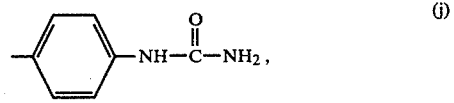 (j)

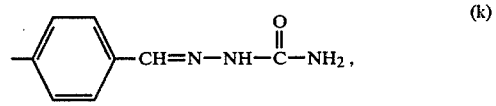 (k)

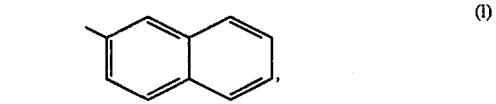 (l)

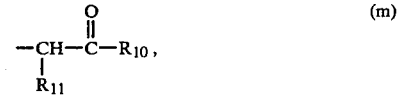 (m)

wherein R$_{10}$ is phenyl, p-bromophenyl, p-biphenylyl, p-nitrophenyl, p-benzamidophenyl, or 2-naphthyl, and wherein R$_{11}$ is hydrogen or benzoyl, or (n) a pharmacologically acceptable cation, wherein R$_9$ is hydrogen, methyl, or ethyl, and R$_{16}$ is hydrogen, alkyl of one to 4 carbon atoms, inclusive, aralkyl of 7 to 12 carbon atoms, inclusive, phenyl, or phenyl substituted with alkyl of one to 4 carbon atoms, inclusive;

wherein R₄ is

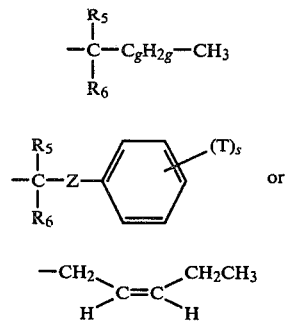

wherein $C_gH_{2g}$ is alkylene of one to 9 carbon atoms, inclusive, with one to 5 carbon atoms, inclusive, in the chain between —CR₅R₆— and terminal methyl, wherein R₅ and R₆ are hydrogen, alkyl of one to 4 carbon atoms, inclusive, or fluoro, being the same or different, with the proviso that one of R₅ and R₆ is fluoro only when the other is hydrogen or fluoro and the further proviso that neither R₅ nor R₆ is fluoro when Z is oxa (—O—); wherein Z represents an oxa atom (—O—) or $C_jH_{2j}$ wherein $C_jH_{2j}$ is a valence bond or alkylene of one to 9 carbon atoms, inclusive, with one to 6 carbon atoms, inclusive between CR₅R₆— and the phenyl ring; wherein T is alkyl of one to 4 carbon atoms, inclusive, fluoro, chloro, trifluoromethyl, or —OR₇— wherein R₇ is alkyl of one to 4 carbon atoms, inclusive, and s is zero, one, 2 or 3, with the proviso that not more than two T's are other than alkyl and when s is 2 or 3 the T's are either the same or different; and wherein X is
(1) trans—CH=CH—
(2) cis—CH=CH—
(3) —C≡C— or
(4) —CH₂CH₂—; including the lower alkanoates thereof.

In the formula IV as used herein, attachment to R₂₀ corresponds to bonds to the cyclopentane ring at the C-8, C-9, and C-12 positions following prostaglandin nomenclature, thus:

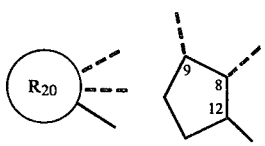

Within the scope of the prostaglandin derivatives described herein there are represented (a) PGF_α compounds when R₂₀ is

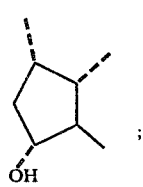

(b) 11β-PGF_α compounds when R₂₀ is

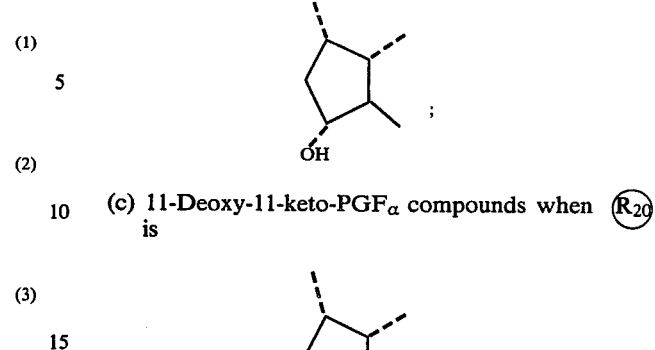

(c) 11-Deoxy-11-keto-PGF_α compounds when R₂₀ is

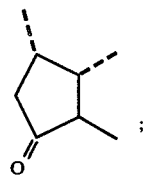

(d) 11-Deoxy-11-methylene-PGF_α compounds when R₂₀ is

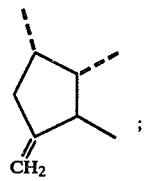

(e) 11-Deoxy-PGF_α compounds when R₂₀ is

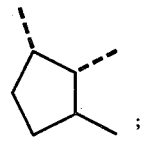

(f) 11-Deoxy-10,11-Didehydro-PGF_α compounds when R₂₀ is

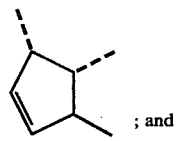

; and (g) 11-Deoxy-11-hydroxymethyl-PGF_α compounds when R₂₀ is

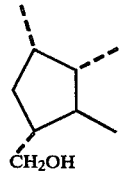

For those compounds of formula IV wherein Q is

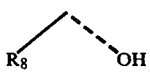

i.e. wherein the C-15 hydroxyl group is attached to the side chain in alpha configuration, the configuration at C-15 is identical with that of the naturally occuring prostaglandins such as PGE₁ obtained from mammalian tissues. The 15-epimer compounds are represented by formula IV when Q is

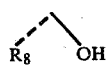

and are identified variously as "15-epi" or "15β" or "15R" by the appropriate prefix in the name. As is known in the art, "R" and "S" designations depend on the neighboring substituents. See R. S. Cahn, J. Chem. Ed. 41, 116 (1964).

An example of the enol ethers of formula IV is represented by the formula

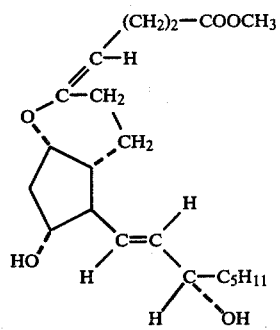

VIII named (4Z)-9-deoxy-5,9α-epoxy-Δ$^4$-PGF$_1$, methyl ester.

As to the "Z" and "E" nomenclature for stereoisomerism about a double bond, see for example J. E. Blackwood et al., J. Am. Chem. Soc. 90, 509 (1968).

Also included within the scope of this invention are compounds of the formula

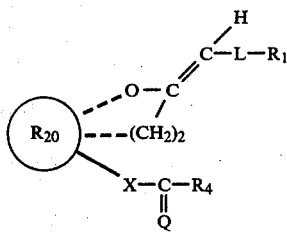

XXVIII wherein L, Q, R$_1$, R$_4$, R$_{20}$ and X are as defined herein.

I claim:

1. A 4Z compound of the formula

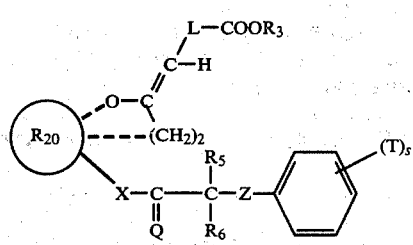

wherein R$_{20}$ is

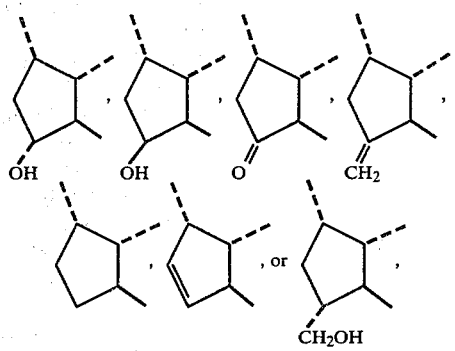

wherein

L is —(CH$_2$)$_d$—C(R$_2$)$_2$— wherein d is zero to 5, R$_2$ is hydrogen, methyl, or fluoro, being the same or different with the proviso that one R$_2$ is not methyl when the other is fluoro, wherein Q is

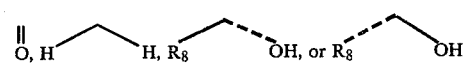

wherein R$_8$ is hydrogen or alkyl of one to 4 carbon atoms, inclusive, wherein R$_3$ is (a) hydrogen (b) alkyl of one to 12 carbon atoms, inclusive, or (c) cycloalkyl of 3 to 10 carbon atoms, inclusive, (d) aralkyl of 7 to 12 carbon atoms, inclusive, (e) phenyl, (f) phenyl substituted with one, 2, or 3 chloro or alkyl of one to 4 carbon atoms, inclusive,

(g)

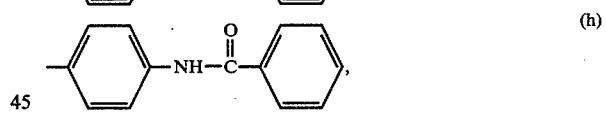

(h)

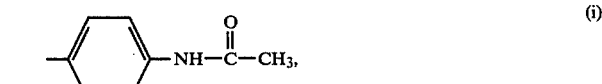

(i)

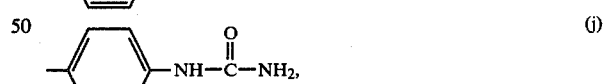

(j)

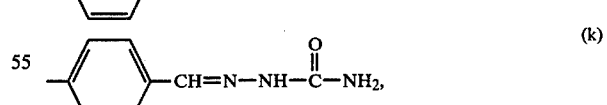

(k)

(l)

(m)

wherein R$_{10}$ is phenyl, p-bromophenyl, p-biphenylyl, p-nitrophenyl, p-benzamidophenyl, or 2-naphthyl, and wheren $R_{11}$ is hydrogen or benzoyl, or (n) a pharmacologically acceptable cation;

wherein $R_5$ and $R_6$ are hydrogen, alkyl of one to 4 carbon atoms, inclusive, or fluoro, being the same or different, with the proviso that one of $R_5$ and $R_6$ is fluoro only when the other is hydrogen or fluoro and the further proviso that neither $R_5$ nor $R_6$ is fluoro when Z is oxa (—O—); wherein Z represents an oxa atom (—O—), a valence bond or alkylene of one to 9 carbon atoms, inclusive, with one to 6 carbon atoms, inclusive between $CR_5R_6$— and the phenyl ring;

wherein T is alkyl of one to 4 carbon atoms, inclusive, fluoro, chloro, trifluoromethyl, or —$OR_7$— wherein $R_7$ is alkyl of one to 4 carbon atoms, inclusive, and s is zero, one, 2 or 3, with the proviso that not more than two T's are other than alkyl and when s is 2 or 3 the T's are either the same or different; and wherein X is
(1) trans—CH=CH—
(2) cis—CH=CH—
(3) —C≡C— or
(4) —CH$_2$CH$_2$—;
including the lower alkanoates thereof.

2. A compound according to claim 1 wherein $R_{20}$ is

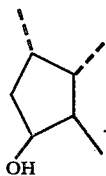

3. A compound according to claim 1 wherein $R_{20}$ is

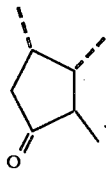

4. A compound according to claim 1 wherein $R_{20}$ is

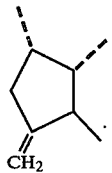

5. A compound according to claim 1 wherein $R_{20}$ is

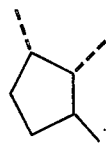

6. A compound according to claim 1 wherein $R_{20}$ is

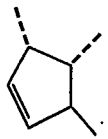

7. A compound according to claim 1 wherein $R_{20}$ is

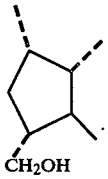

8. A compound according to claim 1 wherein $R_{20}$ is

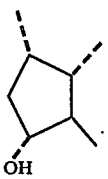

9. A compound according to claim 8 wherein L is —(CH$_2$)$_n$—, n being 2, 3, or 4, and wherein Q is

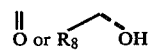

wherein $R_8$ is hydrogen, methyl, or ethyl.

10. A compound according to claim 9 wherein L is —CH$_2$CH$_2$—.

11. A compound according to claim 10 wherein $R_5$ and $R_6$ are hydrogen.

12. A compound according to claim 11 wherein "s" is zero.

13. A compound according to claim 12 wherein X is —C≡C—.

14. A compound according to claim 12 wherein X is —CH$_2$CH$_2$—.

15. A compound according to claim 13 wherein $R_3$ is hydrogen, alkyl of one to 4 carbon atoms, inclusive, or sodium.

16. A compound according to claim 12 wherein X is trans—CH=CH—.

17. (4Z)-9-Deoxy-5,9α-epoxy-Δ$^4$-17-phenyl-18,19,20-trinor-13,14-didehydro-PGF$_1$, methyl ester, a compound according to claim 15.

18. (4Z)-9-Deoxy-5,9α-epoxy-Δ$^4$-16-phenoxy-17,18,19,20-tetranor-13,14-didehydro-PGF$_1$, methyl ester, a compound according to claim 15.

19. A compound according to claim 14, wherein $R_3$ is hydrogen, alkyl of one to 4 carbon atoms, inclusive, or sodium.

20. A compound according to claim 19, wherein $R_3$ is methyl.

21. (4Z)-9-Deoxy-5,9α-epoxy-Δ$^4$-17-phenyl-18,19,20-trinor-13,14-dihydro-PGF$_1$, methyl ester, a compound according to claim 20.

22. (4Z)-9-Deoxy-5,9α-epoxy-$\Delta^4$-16-phenoxy-17,18,19,20-tetranor-13,14-dihydro-PGF$_1$, methyl ester, a compound according to claim 20.

23. A compound according to claim 19, wherein R$_3$ is sodium.

24. A compound according to claim 16, wherein R$_3$ is hydrogen, alkyl of one to 4 carbon atoms, inclusive, or sodium.

25. A compound according to claim 24, wherein R$_3$ is methyl.

26. (4Z)-9-Deoxy-5,9α-epoxy-$\Delta^4$-16-phenoxy-17,18,19,20-tetranor-PGF$_1$, methyl ester, a compound according to claim 25.

27. A compound according to claim 24, wherein R$_3$ is sodium.

28. (4Z)-9-Deoxy-5,9α-epoxy-$\Delta^4$-17-phenyl-18,19,20-trinor-PGF$_1$, methyl ester, a compound according to claim 25.

29. A compound according to claim 12, wherein X is cis—CH=CH—.

30. A compound according to claim 29, wherein R$_3$ is hydrogen, alkyl of one to 4 carbon atoms, inclusive, or sodium.

31. (4Z)-9-Deoxy-5,9α-epoxy-$\Delta^4$-17-phenyl-18,19,20-trinor-cis-13-PGF$_1$, methyl ester, a compound according to claim 30.

32. (4Z)-9-Deoxy-5,9α-epoxy-$\Delta^4$-16-phenoxy-17,18,19,20-tetranor-cis-13-PGF$_1$, methyl ester, a compound according to claim 30.

33. A compound according to claim 11, wherein "s" is one.

34. A compound according to claim 33, wherein X is —CH$_2$CH$_2$—.

35. A compound according to claim 34, wherein R$_3$ is hydrogen, alkyl of one to 4 carbon atoms, inclusive, or sodium.

36. (4Z)-9-Deoxy-5,9α-epoxy-$\Delta^4$-16-(m-trifluoromethylphenoxy)-17,18,19,20-tetranor-13,14-dihydro-PGF$_1$, methyl ester, a compound according to claim 35.

37. (4Z)-9-Deoxy-5,9α-epoxy-$\Delta^4$-16-(m-chlorophenoxy)-17,18,19,20-tetranor-13,14-dihydro-PGF$_1$, methyl ester, a compound according to claim 35.

38. (4Z)-9-Deoxy-5,9α-epoxy-$\Delta^4$-16-(p-fluorophenoxy)-17,18,19,20-tetranor-13,14-dihydro-PGF$_1$, methyl ester, a compound according to claim 35.

39. A compound according to claim 33, wherein X is trans—CH=CH—.

40. A compound according to claim 39, wherein R$_3$ is hydrogen, alkyl of one to 4 carbon atoms, inclusive, or sodium.

41. A compound according to claim 40, wherein R$_3$ is methyl.

42. (4Z)-9-Deoxy-5,9α-epoxy-$\Delta^4$-16-(m-trifluoromethylphenoxy)-17,18,19,20-tetranor-PGF$_1$, methyl ester, a compound according to claim 41.

43. (4Z)-9-Deoxy-5,9α-epoxy-$\Delta^4$-16-(m-chlorophenoxy)-17,18,19,20-tetranor-PGF$_1$, methyl ester, a compound according to claim 41.

44. (4Z)-9-Deoxy-5,9α-epoxy-$\Delta^4$-16-(p-fluorophenoxy)-17,18,19,20-tetranor-PGF$_α$, methyl ester, a compound according to claim 41.

45. A compound according to claim 40, wherein R$_3$ is sodium.

46. A compound according to claim 33, wherein X is cis—CH=CH—.

47. A compound according to claim 46, wherein R$_3$ is hydrogen, alkyl of one to 4 carbon atoms, inclusive, or sodium.

48. (4Z)-9-Deoxy-5,9α-epoxy-$\Delta^4$-16-(m-trifluoromethylphenoxy)-17,18,19,20-tetranor-cis-13-PGF$_1$, methyl ester, a compound according to claim 47.

49. A compound according to claim 10, wherein R$_5$ and R$_6$ are methyl.

50. A compound according to claim 49, wherein "s" is zero.

51. A compound according to claim 50, wherein X is —CH$_2$CH$_2$—.

52. A compound according to claim 51, wherein R$_3$ is hydrogen, alkyl of one to 4 carbon atoms, inclusive, or sodium.

53. (4Z)-9-Deoxy-5,9α-epoxy-$\Delta^4$-16,16-dimethyl-17-phenyl-18,19,20-trinor-13,14-dihydro-PGF$_1$, methyl ester, a compound according to claim 52.

54. A compound according to claim 50, wherein X is trans—CH=CH—.

55. A compound according to claim 54, wherein R$_3$ is hydrogen, alkyl of one to 4 carbon atoms, inclusive, or sodium.

56. A compound according to claim 55, wherein R$_3$ is methyl.

57. (4Z)-9-Deoxy-5,9α-epoxy-$\Delta^4$-16,16-dimethyl-17-phenyl-18,19,20-trinor-PGF$_1$, methyl ester, a compound according to claim 56.

58. (4Z)-9-Deoxy-5,9α-epoxy-$\Delta^4$-16-methyl-16-phenoxy-18,19,20-trinor-PGF$_1$, methyl ester, a compound according to claim 56.

59. A compound according to claim 55, wherein R$_3$ is sodium.

60. A compound according to claim 50, wherein X is cis—CH=CH—.

61. A compound according to claim 60, wherein R$_3$ is hydrogen, alkyl of one to 4 carbon atoms, inclusive, or sodium.

62. (4Z)-9-Deoxy-5,9α-epoxy-$\Delta^4$-16,16-dimethyl-17-phenyl-18,19,20-trinor-cis-13-PGF$_1$, methyl ester, a compound according to claim 61.

63. A compound according to claim 10, wherein R$_5$ and R$_6$ are fluoro.

64. A compound according to claim 63, wherein "s" is zero.

65. A compound according to claim 64, wherein X is —CH$_2$CH$_2$—.

66. A compound according to claim 65, wherein R$_3$ is hydrogen, alkyl of one to 4 carbon atoms, inclusive, or sodium.

67. (4Z)-9-Deoxy-5,9α-epoxy-$\Delta^4$-16,16-difluoro-17-phenyl-18,19,20-trinor-13,14-dihydro-PGF$_1$, methyl ester, a compound according to claim 66.

68. A compound according to claim 64, wherein X is trans—CH=CH—.

69. A compound according to claim 68, wherein R$_3$ is hydrogen, alkyl of one to 4 carbon atoms, inclusive, or sodium.

70. (4Z)-9-Deoxy-5,9α-epoxy-$\Delta^4$-16,16-difluoro-17-phenyl-18,19,20-trinor-PGF$_1$, methyl ester, a compound according to claim 69.

71. A compound according to claim 8, wherein L is —CH$_2$CF$_2$— and wherein Q is

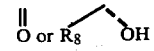

wherein R$_8$ is hydrogen, methyl, or ethyl.

72. A compound according to claim 71, wherein R$_5$ and R$_6$ are hydrogen.

73. A compound according to claim 72, wherein "s" is zero.

74. A compound according to claim 73, wherein X is —CH$_2$CH$_2$—.

75. A compound according to claim 74, wherein R$_3$ is hydrogen, alkyl of one to 4 carbon atoms, inclusive, or sodium.

76. (4Z)-9-Deoxy-5,9α-epoxy-Δ$^4$-2,2-difluoro-16-phenoxy-17,18,19,20-tetranor-13,14-dihydro-PGF$_1$, methyl ester, a compound according to claim 75.

77. A compound according to claim 73, wherein X is trans—CH=CH—.

78. A compound according to claim 77, wherein R$_3$ is hydrogen, alkyl of one to 4 carbon atoms, inclusive, or sodium.

79. A compound according to claim 78, wherein R$_3$ is methyl.

80. (4Z)-9-Deoxy-5,9α-epoxy-Δ$^4$-2,2-difluoro-17-phenyl-18,19,20-trinor-PGF$_1$, methyl ester, a compound according to claim 79.

81. (4Z)-9-Deoxy-5,9α-epoxy-Δ$^4$-2,2-difluoro-16-phenoxy-17,18,19,20-tetranor-PGF$_1$, methyl ester, a compound according to claim 79.

82. A compound according to claim 78, wherein R$_3$ is sodium.

83. A compound according to claim 73, wherein X is cis—CH=CH—.

84. A compound according to claim 83, wherein R$_3$ is hydrogen, alkyl of one to 4 carbon atoms, inclusive, or sodium.

85. (4Z)-9-Deoxy-5,9α-epoxy-Δ$^4$-2,2-difluoro-16-phenoxy-17,18,19,20-tetranor-cis-13-PGF$_1$, methyl ester, a compound according to claim 84.

86. A compound according to claim 71, wherein R$_5$ and R$_6$ are methyl.

87. A compound according to claim 86, wherein "s" is zero.

88. A compound according to claim 87, wherein X is —CH$_2$CH$_2$—.

89. A compound according to claim 88, wherein R$_3$ is hydrogen, alkyl of one to 4 carbon atoms, inclusive, or sodium.

90. (4Z)-9-Deoxy-5,9α-epoxy-Δ$^4$-2,2-difluoro-16-methyl-16-phenoxy-18,19,20-trinor-13,14-dihydro-PGF$_1$, methyl ester, a compound according to claim 89.

91. A compound according to claim 87, wherein X is trans—CH=CH—.

92. A compound according to claim 91, wherein R$_3$ is hydrogen, alkyl of one to 4 carbon atoms, inclusive, or sodium.

93. (4Z)-9-Deoxy-5,9α-epoxy-Δ$^4$-2,2-difluoro-16-methyl-16-phenoxy-18,19,20-trinor-PGF$_1$, methyl ester, a compound according to claim 92.

94. A compound according to claim 87, wherein X is cis—CH=CH—.

95. A compound according to claim 94, wherein R$_3$ is hydrogen, alkyl of one to 4 carbon atoms, inclusive, or sodium.

96. (4Z)-9-Deoxy-5,9α-epoxy-Δ$^4$-2,2-difluoro-16-methyl-16-phenoxy-18,19,20-trinor-cis-13-PGF$_1$, methyl ester, a compound according to claim 95.

97. A 4E compound of the formula

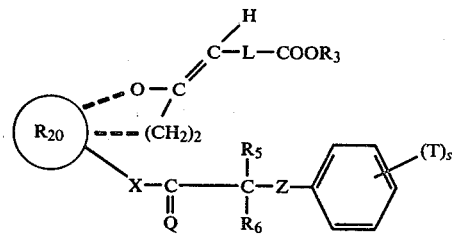

wherein R$_{20}$ is

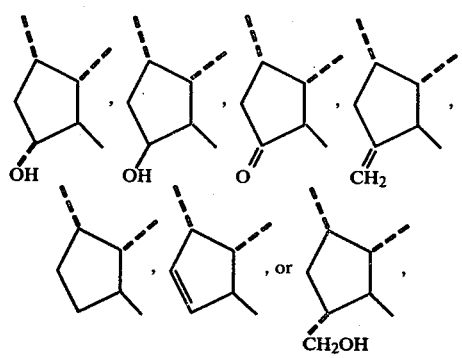

wherein L is —(CH$_2$)$_d$—C(R$_2$)$_2$— wherein d is zero to 5, R$_2$ is hydrogen, methyl, or fluoro, being the same or different with the proviso that one R$_2$ is not methyl when the other is fluoro, wherein Q is

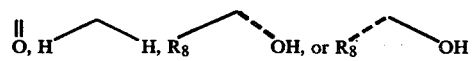

wherein R$_8$ is hydrogen or alkyl of one to 4 carbon atoms, inclusive, wherein R$_3$ is (a) hydrogen, (b) alkyl of one to 12 carbon atoms, inclusive, (d) aralkyl of 7 to 12 carbon atoms, inclusive, (e) phenyl, (f) phenyl substituted with one, 2, or 3 chloro or alkyl of one to 4 carbon atoms, inclusive,

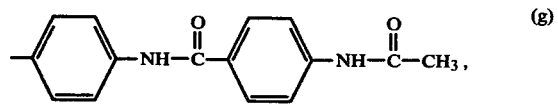 (g)

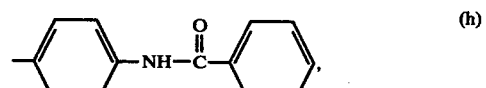 (h)

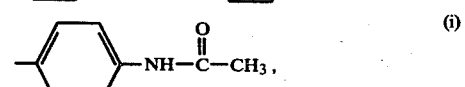 (i)

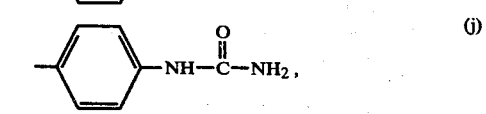 (j)

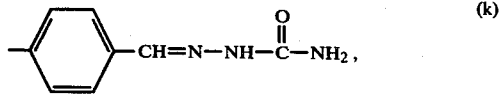 (k)

-continued

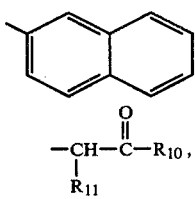
(l)

(m)

wherein R$_{10}$ is phenyl, p-bromophenyl, p-biphenylyl, p-nitrophenyl, p-benzamidophenyl, or 2-naphthyl, and wherein R$_{11}$ is hydrogen or benzoyl, or (n) a pharmacologically acceptable cation;

wherein R$_5$ and R$_6$ are hydrogen, alkyl of one to 4 carbon atoms, inclusive, or fluoro, being the same or different, with the proviso that one of R$_5$ and R$_6$ is fluoro only when the other is hydrogen or fluoro and the further proviso that neither R$_5$ nor R$_6$ is fluoro when Z is oxa (—O—); wherein Z represents an oxa atom (—O—), a valence bond or alkylene of one to 9 carbon atoms, inclusive, with one to 6 carbon atoms, inclusive between CR$_5$R$_6$— and the phenyl ring;

wherein T is alkyl of one to 4 carbon atoms, inclusive, fluoro, chloro, trifluoromethyl, or —OR$_7$— wherein R$_7$ is alkyl of one to 4 carbon atoms, inclusive, and s is zero, one, 2 or 3, with the proviso that not more than two T's are other than alkyl and when s is 2 or 3 the T's are either the same or different; and wherein X is
(1) trans—CH=CH—
(2) cis—CH=CH—
(3) —C≡C— or
(4) —CH$_2$CH$_2$—; including the lower alkanoates thereof.

* * * * *

UNITED STATES PATENT OFFICE
CERTIFICATE OF CORRECTION

Patent No. 4,210,748          Dated  1 July 1980

Inventor(s)  Roy A. Johnson

It is certified that error appears in the above-identified patent and that said Letters Patent are hereby corrected as shown below:

In the Abstract, line 1, "($PG_1$," should read -- ($PG_1$), --; that portion of the first formula reading

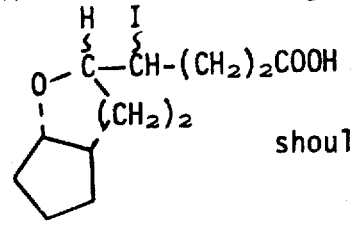   should read   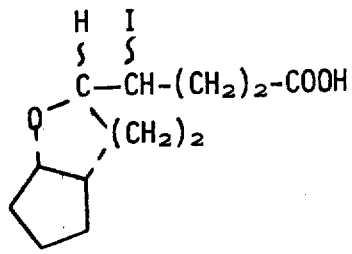

Column 2, lines 4-7,

" 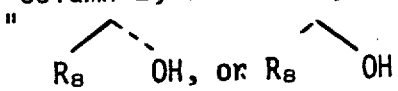 " should read -- 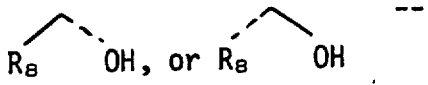 --

Column 2, line 64, "and $R_{16}$ is" should read -- and $R_{18}$ is --;
Column 4, lines 1-8

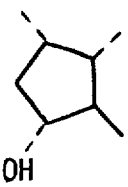   should read   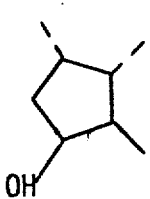

Signed and Sealed this

Twenty-fourth Day of March 1981

[SEAL]

Attest:

RENE D. TEGTMEYER

Attesting Officer        Acting Commissioner of Patents and Trademarks